United States Patent [19]
Jofuku et al.

[11] Patent Number: 5,994,622
[45] Date of Patent: Nov. 30, 1999

[54] METHODS FOR IMPROVING SEEDS

[75] Inventors: K. Diane Jofuku; Jack K. Okamuro, both of Santa Cruz, Calif.

[73] Assignee: The Regents of the University of California, Oakland, Calif.

[21] Appl. No.: 08/700,152

[22] Filed: Aug. 20, 1996

[51] Int. Cl.⁶ .......................... C12N 15/00; C12N 15/29; A01H 5/10; A01H 5/00
[52] U.S. Cl. .......................... 800/260; 800/262; 800/264; 800/270; 800/281; 800/284; 800/285; 800/286; 800/287; 800/290; 800/306; 800/312; 435/468; 435/415; 435/419
[58] Field of Search .................................. 435/172.3, 468, 435/415, 419; 47/58; 800/260, 262, 264, 270, 281, 284–287, 290, 306, 312, 205, 250, 255

[56] References Cited

PUBLICATIONS

Irish and Sussex *Plant Cell* :741–753 (1990).
Bowman, *Flowering Newsletter* 14:7–19 (1992).
Huala and Sussex *Plant Cell* 4:901+–913 (1992).
Bowman et al., *Development* 119–721–743 (1993).
Schultz and Haughn, *Development* 119:745–765 (1993).
Shannon and Meeks–Wagner, *Plant Cell* 5:639–655 (1993).
Bowman et al., *Development* 112:1–20 (1991).
Bowman et al., *Plant Cell* 3:749–758 (1991).
Drews et al., *Cell* 65:91–1002 (1991).
Jack et al. *Cell* 68:683–697 (1992).
Mandel et al. *Cell* 71: 133–143 (1992).
Komaki et al., *Development* 104:195–203 (1988).
Bowman et al., *Plant Cell* 1:37–52 (1989).
Kunst et al., *Plant Cell* 1:1195–1208 (1989).
Jofuku et al., *The Plant Cell* 6:1211–1225 (1994).
Leon–Kloosterziel et al. *The Plant Cell* 6:385–392 (1994).
Mizukami and Ma *Cell* 71:119–131 (1992).
*Arabidopsis: An Atlas of Morphology and Development* Bowman, J. ed. pp. 351 to 401 (Springer–Verlag New York, 1994).

*Primary Examiner*—Mary E. Mosher
*Attorney, Agent, or Firm*—Townsend and Townsend and Crew

[57] ABSTRACT

The invention provides methods of modulating seed mass and other traits in plants. The methods involve producing transgenic plants comprising a recombinant expression cassette containing an AP2 nucleic acid linked to a plant promoter.

35 Claims, 2 Drawing Sheets

Figure I. The AP2 domain

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 67 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Domain
      (B) LOCATION: 1..67
      (D) OTHER INFORMATION: /note= "APETALA 2 (AP2) of Arabidopsis
         direct repeat domain AP2-R1 consisting
         of amino acids 129-195 of the AP2
         protein"

(xi) SEQUENCE DESCRIPTION: SEQ ID NO:1:

```
Ser Ser Gln Tyr Arg Gly Val Thr Phe Tyr Arg Arg Thr Gly Arg Trp
1               5                   10                  15

Glu Ser His Ile Trp Asp Cys Gly Lys Gln Val Tyr Leu Gly Gly Phe
            20                  25                  30

Asp Thr Ala His Ala Ala Ala Arg Ala Tyr Asp Arg Ala Ala Ile Lys
        35                  40                  45

Phe Arg Gly Val Glu Ala Asp Ile Asn Phe Asn Ile Asp Tyr Asp
    50                  55                  60
```

Asp Asp Leu
65

(2) INFORMATION FOR SEQ ID NO:2:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Domain
        (B) LOCATION: 1..68
        (D) OTHER INFORMATION: /note= "APETALA 2 (AP2) of Arabidopsis
            direct repeat domain AP2-R2 consisting
            of amino acids 221-288 of the AP2
            protein"

(xi) SEQUENCE DESCRIPTION: SEQ ID NO:2:

```
Ser Ser Lys Tyr Arg Gly Val Thr Leu His Lys Cys Gly Arg Trp Glu
1               5                  10                  15

Ala Arg Met Gly Gln Phe Leu Gly Lys Lys Tyr Val Tyr Leu Gly Leu
            20                  25                  30

Phe Asp Thr Glu Val Glu Ala Arg Ala Tyr Asp Lys Ala Ala Ile
        35                  40                  45

Lys Cys Asn Gly Lys Asp Ala Val Thr Asn Phe Asp Pro Ser Ile Tyr
    50                  55                  60

Asp Glu Glu Leu
65
```

(2) INFORMATION FOR SEQ ID NO:3:

(i) SEQUENCE CHARACTERISTICS:
        (A) LENGTH: 1680 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 190..1488
        (D) OTHER INFORMATION: /product= "APETALA 2 (AP2)"

(xi) SEQUENCE DESCRIPTION: SEQ ID NO:3:

```
CTCTCTCTCT CTCTTTAGCT CTTTTTTTTT TTTTGTTTTC ATTAAAGTTT TTATTTTATT      60

TTCTACCAAC CAAAAGCTTT TCTCTTTGGT TTCTCTTATT TAGCTTCTAA CCTTGAGGAG     120

AATATACCAG AGGATTGAAG TTTGAACCTT CAAAGATCAA AATCAAGAAA CCAAAAAAAA     180

ACAAAAAAA ATG TGG GAT CTA AAC GAC GCA CCA CAC CAA ACA CAA AGA        228
           Met Trp Asp Leu Asn Asp Ala Pro His Gln Thr Gln Arg
               1               5                  10

GAA GAA GAA TCT GAA GAG TTT TGT TAT TCT TCA CCA AGT AAA CGG GTT     276
Glu Glu Glu Ser Glu Glu Phe Cys Tyr Ser Ser Pro Ser Lys Arg Val
    15                  20                  25

GGA TCT TTC TCT AAT TCA AGC TCT TCA GCT GTT GTT ATC GAA GAT GGA     324
Gly Ser Phe Ser Asn Ser Ser Ser Ser Ala Val Val Ile Glu Asp Gly
    30                  35                  40                  45

TCC GAT GAC GAT GAA CTT AAC CGG GTC AGA CCC AAT AAC CCA CTT GTC     372
Ser Asp Asp Asp Glu Leu Asn Arg Val Arg Pro Asn Asn Pro Leu Val
            50                  55                  60
```

-continued

| | | |
|---|---|---|
| ACC CAT CAG TTC TTC CCT GAG ATG GAT TCT AAC GGC GGT GGT GTT GCT<br>Thr His Gln Phe Phe Pro Glu Met Asp Ser Asn Gly Gly Gly Val Ala<br>              65                     70                  75 | 420 |
| TCT GGC TTT CCT CGG GCT CAC TGG TTT GGT GTT AAG TTT TGT CAG TCG<br>Ser Gly Phe Pro Arg Ala His Trp Phe Gly Val Lys Phe Cys Gln Ser<br>        80                     85                     90 | 468 |
| GAT CTA GCC ACC GGA TCG TCC GCG GGT AAA GCT ACC AAC GTT GCC GCT<br>Asp Leu Ala Thr Gly Ser Ser Ala Gly Lys Ala Thr Asn Val Ala Ala<br>     95                      100                  105 | 516 |
| GCC GTA GTG GAG CCG GCA CAG CCG TTG AAA AAG AGT CGG CGT GGA CCA<br>Ala Val Val Glu Pro Ala Gln Pro Leu Lys Lys Ser Arg Arg Gly Pro<br>110                     115                  120                  125 | 564 |
| AGA TCA AGA AGT TCT CAG TAT AGA GGT GTT ACG TTT TAC CGG CGT ACC<br>Arg Ser Arg Ser Ser Gln Tyr Arg Gly Val Thr Phe Tyr Arg Arg Thr<br>               130                    135                  140 | 612 |
| GGA AGA TGG GAA TCT CAT ATT TGG GAC TGT GGG AAA CAA GTT TAC TTA<br>Gly Arg Trp Glu Ser His Ile Trp Asp Cys Gly Lys Gln Val Tyr Leu<br>               145                    150                  155 | 660 |
| GGT GGA TTT GAC ACT GCT CAT GCA GCA GCT CGA GCA TAT GAT AGA GCT<br>Gly Gly Phe Asp Thr Ala His Ala Ala Ala Arg Ala Tyr Asp Arg Ala<br>             160                    165                  170 | 708 |
| GCT ATT AAA TTC CGT GGA GTA GAA GCG GAT ATC AAT TTC AAC ATC GAC<br>Ala Ile Lys Phe Arg Gly Val Glu Ala Asp Ile Asn Phe Asn Ile Asp<br>175                     180                  185 | 756 |
| GAT TAT GAT GAT GAC TTG AAA CAG ATG ACT AAT TTA ACC AAG GAA GAG<br>Asp Tyr Asp Asp Asp Leu Lys Gln Met Thr Asn Leu Thr Lys Glu Glu<br>190                     195                  200                  205 | 804 |
| TTC GTA CAC GTA CTT CGC CGA CAA AGC ACA GGC TTC CCT CGA GGA AGT<br>Phe Val His Val Leu Arg Arg Gln Ser Thr Gly Phe Pro Arg Gly Ser<br>             210                    215                  220 | 852 |
| TCG AAG TAT AGA GGT GTC ACT TTG CAT AAG TGT GGT CGT TGG GAA GCT<br>Ser Lys Tyr Arg Gly Val Thr Leu His Lys Cys Gly Arg Trp Glu Ala<br>             225                    230                  235 | 900 |
| CGT ATG GGT CAA TTC TTA GGC AAA AAG TAT GTT TAT TTG GGT TTG TTC<br>Arg Met Gly Gln Phe Leu Gly Lys Lys Tyr Val Tyr Leu Gly Leu Phe<br>             240                    245                  250 | 948 |
| GAC ACC GAG GTC GAA GCT GCT AGA GCT TAC GAT AAA GCT GCA ATC AAA<br>Asp Thr Glu Val Glu Ala Ala Arg Ala Tyr Asp Lys Ala Ala Ile Lys<br>             255                    260                  265 | 996 |
| TGT AAC GGC AAA GAC GCC GTG ACC AAC TTT GAT CCG AGT ATT TAC GAT<br>Cys Asn Gly Lys Asp Ala Val Thr Asn Phe Asp Pro Ser Ile Tyr Asp<br>270                     275                  280                  285 | 1044 |
| GAG GAA CTC AAT GCC GAG TCA TCA GGG AAT CCT ACT ACT CCA CAA GAT<br>Glu Glu Leu Asn Ala Glu Ser Ser Gly Asn Pro Thr Thr Pro Gln Asp<br>             290                    295                  300 | 1092 |
| CAC AAC CTC GAT CTG AGC TTG GGA AAT TCG GCT AAT TCG AAG CAT AAA<br>His Asn Leu Asp Leu Ser Leu Gly Asn Ser Ala Asn Ser Lys His Lys<br>             305                    310                  315 | 1140 |
| AGT CAA GAT ATG CGG CTC AGG ATG AAC CAA CAA CAA CAA GAT TCT CTC<br>Ser Gln Asp Met Arg Leu Arg Met Asn Gln Gln Gln Gln Asp Ser Leu<br>             320                    325                  330 | 1188 |
| CAC TCT AAT GAA GTT CTT GGA TTA GGT CAA ACC GGA ATG CTT AAC CAT<br>His Ser Asn Glu Val Leu Gly Leu Gly Gln Thr Gly Met Leu Asn His<br>             335                    340                  345 | 1236 |
| ACT CCC AAT TCA AAC CAC CAA TTT CCG GGC AGC AGC AAC ATT GGT AGC<br>Thr Pro Asn Ser Asn His Gln Phe Pro Gly Ser Ser Asn Ile Gly Ser<br>350                     355                  360                  365 | 1284 |
| GGA GGC GGA TTC TCA CTG TTT CCG GCG GCT GAG AAC CAC CGG TTT GAT<br>Gly Gly Gly Phe Ser Leu Phe Pro Ala Ala Glu Asn His Arg Phe Asp<br>             370                    375                  380 | 1332 |

```
GGT CGG GCC TCG ACG AAC CAA GTG TTG ACA AAT GCT GCA GCA TCA TCA      1380
Gly Arg Ala Ser Thr Asn Gln Val Leu Thr Asn Ala Ala Ala Ser Ser
            385                 390                 395

GGA TTC TCT CCT CAT CAT CAC AAT CAG ATT TTT AAT TCT ACT TCT ACT      1428
Gly Phe Ser Pro His His His Asn Gln Ile Phe Asn Ser Thr Ser Thr
        400                 405                 410

CCT CAT CAA AAT TGG CTG CAG ACA AAT GGC TTC CAA CCT CCT CTC ATG      1476
Pro His Gln Asn Trp Leu Gln Thr Asn Gly Phe Gln Pro Pro Leu Met
        415                 420                 425

AGA CCT TCT TGAATCTTTT ATATTTTTAA GGTTTATTAT TATATAAGAA              1525
Arg Pro Ser
430

AAACAAAAAT GAACCTTTGA AATCCCCACA TGTTCTTGGT CATTTCATTA ATCATCGGCT    1585

TATATTTTGC TTATTTTCCC CTAAATCCTC TTGTTAACTT AGGCGAACAA AAAAAATTAA    1645

TGGAAATCTT TTTCCCTCCA TCGGTTACAA AAATA                                1680

(2) INFORMATION FOR SEQ ID NO:4:

(i) SEQUENCE CHARACTERISTICS:
        (A) LENGTH: 432 amino acids
        (B) TYPE: amino acid
        (D) TOPOLOGY: linear (ii) MOLECULE TYPE: protein (xi) SEQUENCE DESCRIPTION: SEQ ID NO:4:

Met Trp Asp Leu Asn Asp Ala Pro His Gln Thr Gln Arg Glu Glu
 1               5                  10                  15

Ser Glu Glu Phe Cys Tyr Ser Ser Pro Ser Lys Arg Val Gly Ser Phe
                20                  25                  30

Ser Asn Ser Ser Ser Ala Val Val Ile Glu Asp Gly Ser Asp Asp
            35                  40                  45

Asp Glu Leu Asn Arg Val Arg Pro Asn Asn Pro Leu Val Thr His Gln
        50                  55                  60

Phe Phe Pro Glu Met Asp Ser Asn Gly Gly Val Ala Ser Gly Phe
65                  70                  75                  80

Pro Arg Ala His Trp Phe Gly Val Lys Phe Cys Gln Ser Asp Leu Ala
                85                  90                  95

Thr Gly Ser Ser Ala Gly Lys Ala Thr Asn Val Ala Ala Val Val
            100                 105                 110

Glu Pro Ala Gln Pro Leu Lys Lys Ser Arg Arg Gly Pro Arg Ser Arg
        115                 120                 125

Ser Ser Gln Tyr Arg Gly Val Thr Phe Tyr Arg Arg Thr Gly Arg Trp
130                 135                 140

Glu Ser His Ile Trp Asp Cys Gly Lys Gln Val Tyr Leu Gly Gly Phe
145                 150                 155                 160

Asp Thr Ala His Ala Ala Arg Ala Tyr Asp Arg Ala Ala Ile Lys
                165                 170                 175

Phe Arg Gly Val Glu Ala Asp Ile Asn Phe Asn Ile Asp Asp Tyr Asp
            180                 185                 190

Asp Asp Leu Lys Gln Met Thr Asn Leu Thr Lys Glu Glu Phe Val His
        195                 200                 205

Val Leu Arg Arg Gln Ser Thr Gly Phe Pro Arg Gly Ser Ser Lys Tyr
    210                 215                 220

Arg Gly Val Thr Leu His Lys Cys Gly Arg Trp Glu Ala Arg Met Gly
225                 230                 235                 240

Gln Phe Leu Gly Lys Lys Tyr Val Tyr Leu Gly Leu Phe Asp Thr Glu
```

-continued

```
                245                      250                         255
Val Glu Ala Ala Arg Ala Tyr Asp Lys Ala Ala Ile Lys Cys Asn Gly
                260                  265                 270

Lys Asp Ala Val Thr Asn Phe Asp Pro Ser Ile Tyr Asp Glu Glu Leu
        275                 280                 285

Asn Ala Glu Ser Ser Gly Asn Pro Thr Thr Pro Gln Asp His Asn Leu
    290                 295                 300

Asp Leu Ser Leu Gly Asn Ser Ala Asn Ser Lys His Lys Ser Gln Asp
305                 310                 315                 320

Met Arg Leu Arg Met Asn Gln Gln Gln Gln Asp Ser Leu His Ser Asn
                325                 330                 335

Glu Val Leu Gly Leu Gly Gln Thr Gly Met Leu Asn His Thr Pro Asn
                340                 345                 350

Ser Asn His Gln Phe Pro Gly Ser Ser Asn Ile Gly Ser Gly Gly Gly
            355                 360                 365

Phe Ser Leu Phe Pro Ala Ala Glu Asn His Arg Phe Asp Gly Arg Ala
        370                 375                 380

Ser Thr Asn Gln Val Leu Thr Asn Ala Ala Ala Ser Ser Gly Phe Ser
385                 390                 395                 400

Pro His His His Asn Gln Ile Phe Asn Ser Thr Ser Thr Pro His Gln
                405                 410                 415

Asn Trp Leu Gln Thr Asn Gly Phe Gln Pro Pro Leu Met Arg Pro Ser
                420                 425                 430
```

METHODS FOR IMPROVING SEEDS

FIELD OF THE INVENTION

The present invention is directed to plant genetic engineering. In particular, it relates to new methods for modulating mass and other properties of plant seeds.

BACKGROUND OF THE INVENTION

The pattern of flower development is controlled by the floral meristem, a complex tissue whose cells give rise to the different organ systems of the flower. Genetic and molecular studies have defined a network of genes that control floral meristem identity and floral organ development in Arabidopsis, snapdragon, and other plant species (see, e.g., Coen and Carpenter, *Plant Cell* 5:1175–1181 (1993) and Okamuro et al., Plant Cell 5:1183–1193 (1993)). In Arabidopsis, a floral homeotic gene APETALA2 (AP2) controls three critical aspects of flower ontogeny—the establishment of the floral meristem (Irish and Sussex, *Plcant Cell* 2:741–753 (1990); Huala and Sussex, *Plant Cell* 4:901–913 (1992); Bowman et al., *Development* 119:721–743 (1993); Schultz and Haughn, *Development* 119:745–765 (1993); Shannon and Meeks-Wagner, *Plant Cell* 5:639–655 (1993)), the specification of floral organ identity (Komaki et al., *Development* 104:195–203 (1988)); Bowman et al., *Plant Cell* 1:37–52 (1989); Kunst et al., *Plant Cell* 1:1195–1208 (1989)), and the temporal and spatial regulation of floral homeotic gene expression (Bowman et al., *Plant Cell* 3:749–758 (1991); Drews et al., *Cell* 65:91–1002 (1991)).

One early function of AP2 during flower development is to promote the establishment of the floral meristem. AP2 performs this function in cooperation with at least three other floral meristem genes, APETALA1 (AP1), LEAFY (LFY), and CAULIFLOWER (CAL) (Irish an Sussex (1990); Bowman, *Flowering Newsletter* 14:7–19 (1992); Huala and Sussex (1992); Bowman et al., (1993); Schultz and Haughn, (1993); Shannon and Meeks-Wagner, (1993)). A second function of AP2 is to regulate floral organ development. In Arabidopsis, the floral meristem produces four concentric rings or whorls of floral organs—sepals, petals, stamens, and carpels. In weak, partial loss-of-function ap2 mutants, sepals are homeotically transformed into leaves, and petals are transformed into pollen-producing stamenoid organs (Bowman et al., *Development* 112:1–20 (1991)). By contrast, in strong ap2 mutants, sepals are transformed into ovule-bearing carpels, petal development is suppressed, the number of stamens is reduced, and carpel fusion is often defective (Bowman et al., (1991)). Finally, the effects of ap2 on floral organ development are in part a result of a third function of AP2, which is to directly or indirectly regulate the expression of several flower-specific homeotic regulatory genes (Bowman et al., *Plant Cell* 3:749–758 (1991); Drews et al., *Cell* 65:91–1002 (1991); Jack et al. *Cell* 68:683–697 (1992); Mandel et al. *Cell* 71: 133–143 (1992)).

Clearly, Ap2 plays a critical role in the regulation of Arabidopsis flower development. Yet, little is known about how it carries out its functions at the cellular and molecular levels. A spatial and combinatorial model has been proposed to explain the role of AP2 and other floral homeotic genes in the specification of floral organ identity(see, e.g., Coen and Carpenter, supra). One central premise of this model is that AP2 and a second floral homeotic gene AGAMOUS (AG) are mutually antagonistic genes. That is, AP2 negatively regulates AG gene expression in sepals and petals, and conversely, AG negatively regulates AP2 gene expression in stamens and carpels. In situ hybridization analysis of AG gene expression in wild-type and ap2 mutant flowers has demonstrated that AP2 is indeed a negative regulator of AG expression. However, it is not yet known how AP2 controls AG. Nor is it known how AG influences AP2 gene activity.

The AP2 gene in Arabidopsis has been isolated by T-DNA insertional mutagenesis as described in Jofuku et al. *The Plant Cell* 6:1211–1225 (1994). AP2 encodes a putative nuclear factor that bears no significant similarity to any known fungal, or animal regulatory protein. Evidence provided there indicates that AP2 gene activity and function are not restricted to developing flowers, suggesting that it may play a broader role in the regulation of Arabidopsis development than originally proposed.

In spite of the recent progress in defining the genetic control of plant development, little progress has been reported in the identification and analysis of genes effecting agronomically important traits such as seed size, protein content, oil content and the like. Characterization of such genes would allow for the genetic engineering of plants with a variety of desirable traits. The present invention addresses these and other needs.

SUMMARY OF THE INVENTION

The present invention provides methods of modulating seed mass and other traits in plants. The methods involve providing a plant comprising a recombinant expression cassette containing an AP2 nucleic acid linked to a plant promoter. The plant is either selfed or crossed with a second plant to produce a plurality of seeds. Seeds with the desired trait (e.g., altered mass) are then selected.

In some embodiments, transcription of the AP2 nucleic acid inhibits expression of an endogenous AP2 gene and the step of selecting includes the step of selecting seed with increased mass or another trait. The seed may have, for instance, increased protein content, carbohydrate content, or oil content. In the case of increased oil content, the types of fatty acids will not be altered as compared to the parental lines. In these embodiments, the AP2 nucleic acid may be linked to the plant promoter in the sense or the antisense orientation. Alternatively, expression of the AP2 nucleic acid may enhance expression of an endogenous AP2 gene and the step of selecting includes the step of selecting seed with decreased mass. This embodiment is particularly useful for producing seedless varieties of crop plants.

If the first plant is crossed with a second plant the two plants may be the same or different species. The plants may be any higher plants, for example, members of the families Brassicaceae or Solanaceae. In some preferred embodiments, the seed are set on the plant comprising the expression cassette containing the AP2 nucleic acid.

In the expression cassettes, the plant promoter may be a constitutive promoter, for example, the CaMV 35S promoter. Alternatively, the promoter may be a tissue-specific promoter. Examples of tissue specific expression useful in the invention include fruit-specific, ovule-specific, seed-specific, integument-specific, or seed coat-specific expression.

The invention also provides seed produced by the methods described above. The seed of the invention comprise a recombinant expression cassette containing an AP2 nucleic acid. If the expression cassette is used to inhibit expression of endogenous AP2 expression, the seed will have a mass at least about 20% greater than the average mass of seeds of the same plant variety which lack the recombinant expression cassette. If the expression cassette is used to enhance expression of AP2, the seed will have a mass at least about 20% less than the average mass of seeds of the same plant variety which lack the recombinant expression cassette. Other traits such as protein content, carbohydrate content, and oil content can be altered in the same manner.

Definitions

The phrase "nticleic acid sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A "heterologous sequence" is one that originates from a foreign species, or, if from the same species, is substantially modified from its original form. For example, a heterologous promoter operably linked to a structural gene is from a species different from that from which the structural gene was derived, or, if from the same species, is substantially modified from its original form.

An "AP2 nucleic acid" or "AP2 polynucleotide sequence" of the invention is a subsequence or full length polynucleotide sequence of a gene which, when present in a transgenic plant, can be used to modlulate seed properties in seed produced by the plant. An exemplary nucleic acid of the invention is the Arabidopsis AP2 sequence as disclosed in Jofuku et al. *The Plant Cell* 6:1211–1225 (1994). The GenBank accession number for this sequence is U12546. An AP2 polynucleotide is typically at least about 30–40 nucleotides to about 3000, usually less than about 5000 nucleotides in length. Usually the nucleic acids are from about 100 to about 2000 nucleotides, often from about 500 to about 1700 nucleotides in length.

AP2 nucleic acids, as explained in more detail below, are a new class of plant regulatory genes that encode AP2 polypeptides, which are distinguished by the presence of a 56–68 amino acid repeated motif, referred to here as the "AP2 domain". The amino acid sequence of an exemplary AP2 polypeptide is shown in Jofuku et al., supra. One of skill will recognize that in light of the present disclosure various modifications (e.g., substitutions, additions, and deletions) can be made to the sequences shown there without substantially affecting its function. These variations are specifically covered by the terms AP2 polypeptide or AP2 polynucleotide.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by the term AP2 nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "AP2 nticleic acid". In addition, the term specifically includes those full length sequences substantially identical (determined as described below) with an AP2 polynucleotide sequence and that encode proteins that retain the function of the AP2 polypeptide (e.g., resulting from conservative substitutions of amino acids in the AP2 polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis., or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 35%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, genomic DNA or cDNA comprising AP2 nucleic acids of the invention can be identified in standard Southern blots under stringent conditions using the cDNA sequence shown in Jofuku et al., supra. For the purposes of this disclosure, stringent conditions for such hybridizations are those which include at least one wash in 0.2×SSC at a temperature of at least about 50° C., usually about 55° C. to about 60° C., for 20 minutes, or equivalent conditions.

DESCRIPTION OF THE PREFERRED EMBODIMENTS

Figure 1:
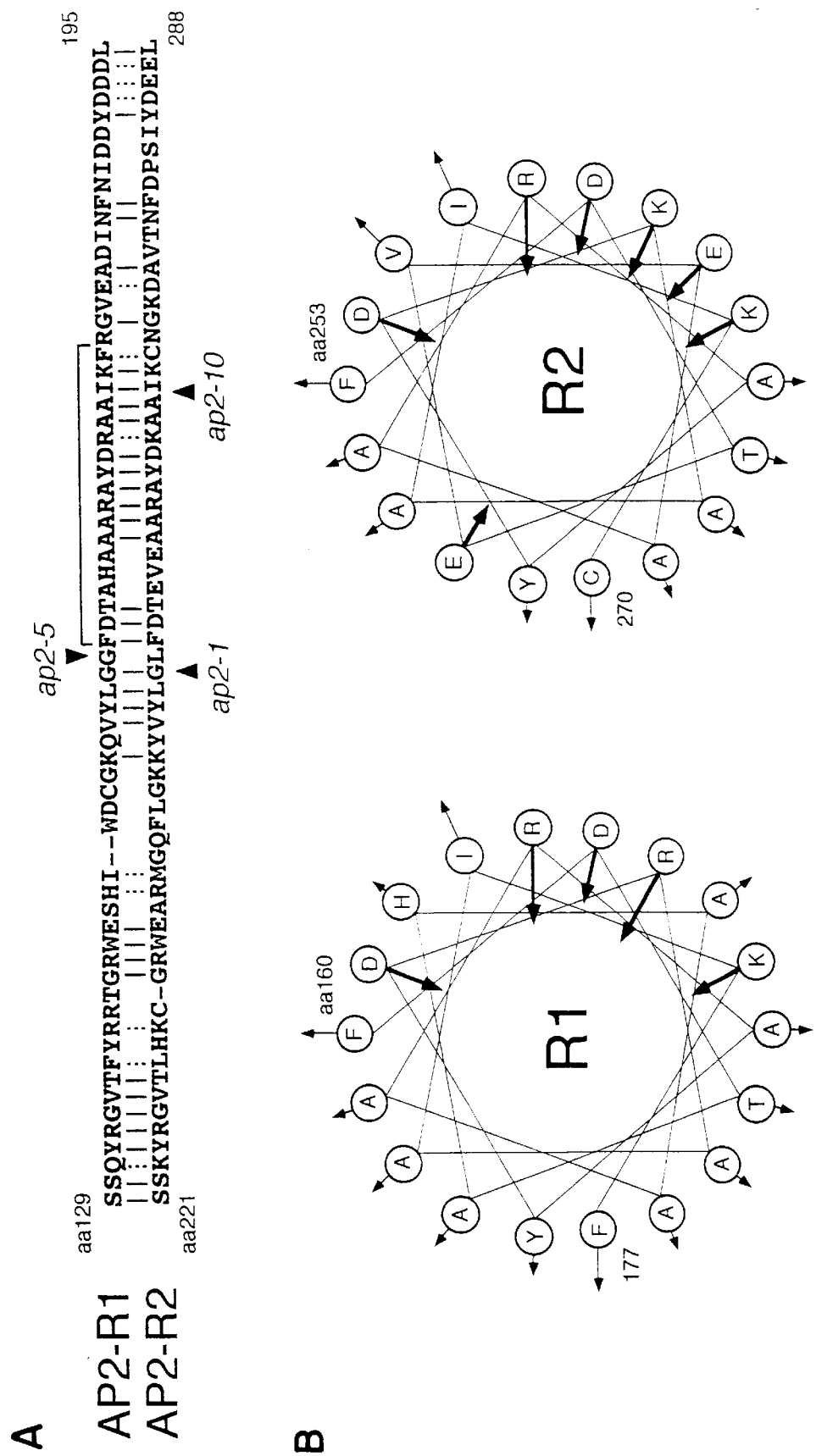
FIG. 1A shows amino acid sequence alignment between AP2 direct repeats AP2-R1 (aa 129–195) (SEQ ID NO:1) and AP2-R2 (aa 221–288) (SEQ ID NO:2). Solid and dashed lines between the two sequences indicate residue identity and similarity, respectively. Arrows indicate the positions of the ap2-1, ap2-5, and ap2-10 mutations described in Jofuku et al. (1994). The bracket above the AP2-R1 and AP2-R2 sequences indicates the residues capable of forming amphipathic a-helices shown in FIG. 1B.
FIG. 1B is a schematic diagram of the putative AP2-R1 (R1) and AP2-R2 (R2) amphipathic a-helices. The NH2 terminal ends of the R1 and R2 helices begin at residues Phe-160 and Phe-253 and rotate clockwise by 100° per residue through Phe-177 and Cys-270, respectively. Arrows directed toward or away from the center of the helical wheel diagrams indicate the negative or positive degree of hydrophobicity as defined by Jones et al. *J. Lipid Res.* 33: 87–296 (1992).

This invention relates to plant AP2 genes, such as the AP2 genes of Arabidopsis. The invention provides molecular strategies for controlling seed size and total seed protein using AP2 overexpression and antisense gene constructs. In particular, transgenic plants containing antisense constructs have dramatically increased seed mass and total seed protein. Alternatively, overexpression of AP2 using a constructs of the invention leads to reduced seed size and total seed protein. Together, data presented here demonstrate that a number of agronomically important traits including seed mass, total seed protein, and oil content, can be controlled in species of agricultural importance.

Isolation of AP2 Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecilcar Cloning—A Laboratory Manual*, Cold Spring Harbor Laboratory, Cold Spring Harbor, N.Y., (1989).

The isolation of AP2 nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as flowers, and a cDNA library which contains the AP2 gene transcript is prepared from the mRNA. Alternatively, cDNA may be prepared from mRNA extracted from other tissues in which AP2 genes or homologs are expressed.

The cDNA or genomic library can then be screened using a probe based upon the sequence of a cloned AP2 gene disclosed here. Probes may be used to hybridize with genomic DNA or cDNA sequences to isolate homologous genes in the same or different plant species. Alternatively, antibodies raised against AP2 can be used to screen an mRNA expression library.

Alternatively, the nucleic acids of interest can be amplified from nucleic acid samples using amplification techniques. For instance, polymerase chain reaction (PCR) technology to amplify the sequences of the AP2 genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying AP2 sequences from plant tissues are generated from comparisons of the sequences provided in Jofuku et al., supra. For a general overview of PCR see *PCR Protocols: A Guide to Methods and Applications*. (Innis, M, Gelfand, D., Sninsky, J. and White, T., eds.), Academnic Press, San Diego (1990).

Polynticleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Suppression of AP2 Activity or Gene Expression

One of skill will recognize that a number of methods can be used to inactivate or suppress AP2 activity or gene expression. The control of the expression can be achieved by introducing mutations into the gene or using recombinant DNA techniques. These techniques are generally well known to one of skill and are discussed briefly below.

Methods for introducing a genetic mutations into a plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Desired mutants are selected by assaying for increased seed mass, oil content and other properties.

Gene expression can be inactivated using recombinant DNA techniques by transforming plant cells with constructs comprising transposons or T-DNA sequences. AP2 mutants prepared by these methods are identified according to standard techniques. For instance, mutants can be detected by PCR or by detecting the presence or absence of AP2 mRNA, e.g., by Northern blots. Mutants can also be selected by assaying for increased seed mass, oil content and other properties.

The isolated sequences prepared as described herein, can also be used in a number of techniques to suppress endogenous AP2 gene expression. A particularly useful gene for this purpose is the AP2 gene described in Jofuku et al., supra.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805–8809 (1988), and Hiatt et al., U.S. Pat. No. 4,801,340.

The nucleic acid segment to be introduced generally will be substantially identical to at least a portion of the endogenous AP2 gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

Catalytic RNA molecules or ribozymes can also be used to inhibit expression of AP2 genes. It is possible to design ribozymes that specifically pair with virtually any target RNA and cleave the phosphodiester backbone at a specific location, thereby functionally inactivating the target RNA.

In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived fronu a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature*, 334:585–591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323, 5,231,020, and 5,283,184.

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

AP2 is believed to form multimers in vivo. As a result, an alternative method for inhibiting AP2 function is through use of dominant negative mutants. This approach involves transformation of plants with constructs encoding mutant AP2 polypeptides that form defective multimers with endogenous wild-type AP2 proteins and thereby inactivate the protein. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate AG is described in Mizukami et al. *Plant Cell* 8:831–845 (1996).

Use of Nucleic Acids of the Invention to Enhance AP2 Gene Expression

Isolated sequences prepared as described herein can also be used to introduce expression of a particular AP2 nucleic acid to enhance or increase endogenous gene expression. Enhanced expression will generally lead to smaller seeds or seedless fruit. Where overexpression of a gene is desired, the desired gene from a different species may be used to decrease potential sense suppression effects.

One of skill will recognize that the polypeptides encoded by the genes of the invention, like other proteins, have different domains which perform different functions. Thus, the gene sequences need not be full length, so long as the desired functional domain of the protein is expressed. The distinguishing features of AP2 polypeptides, including the AP2 domain, are discussed in detail below.

Modified protein chains can also be readily designed utilizing various recombinant DNA techniques well kenown to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virls (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the AP2 nucleic acid in a specific tissue or may be otherwise under more precise environmental or developmental control. Such promoters are referred to here as "inducible" promoters. Examples of environmental conditions that may effect transcription by inducible promoters include anaerobic conditions, elevated temperature, or the presence of light.

Examples of promoters under developmental control include promoters that initiate transcription only in certain tissues, such as fruit, seeds, or flowers. Promoters that direct expression of nucleic acids in ovules, flowers or seeds are particularly useful in the present invention. Examples include the AP2 promoter, a promoter from the ovule-specific BEL1 gene promoter described in Reiser et al. *Cell* 83:735–742

If proper polypeptide expression is desired, a polyadenylation region at the 3'-end of the coding region should be included. The polyaclenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Production of Transpenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

Increasing seed size, protein, amino acid, and oils content is particularly desirable in crop plants in which seed are used directly for animal or human consumption or for industrial purposes. Examples include soybean, canola, and grains such as rice, wheat, corn, rye, and the like. Decreasing seed size, or producing seedless varieties, is particularly important in plants grown for their fruit and in which large seeds may be undesirable. Examples include cucumbers, tomatoes, melons, and cherries.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Since transgenic expression of the nucleic acids of the invention leads to phenotypic changes in seeds and fruit, plants comprising the expression cassettes discussed above must be sexually crossed with a second plant to obtain the final product. The seed of the invention can be derived from a cross between two transgenic plants of the invention, or a cross between a plant of the invention and another plant. The desired effects (e.g., increased seed mass) are generally enhanced when the plant of the invention is the female parent. Without wishing to be bound by theory, it is believed that, because most of the seed (e.g., ovule, endosperm, integument and seed coat) is of maternal origin, altered expression of AP2 in the female parent, as opposed to the male parent leads to enhanced effects.

Seed obtained from plants of the present invention can be analyzed according to well known procedures to identify seed with the desired trait. Increased or decreased size can be determined by weighing seeds or by visual inspection. Protein content is conveniently measured by the method of Bradford et al. *Anal. Bioch.* 72L248 (1976). Oil content is determined using standard procedures such as gas chromatography. These procedures can also be used to confirm that the types of fatty acids and other lipids are not altered in the plants of the invention.

Using these procedures one of skill can identify the seed of the invention by the presence of the expression cassettes of the invention and increased seed mass. Usually, the seed mass will be at least about 10%, often about 20% greater than the average seed mass of plants of the same variety that lack the expression cassette. The mass can be about 50% greater and preferably at least about 75% to about 100% greater. Increases in other properties e.g., protein and oil will be proportional to the increases in mass. Thus, protein or oil content can increase by about 10%, 20%, 50%, 75% or 100% in approximate proportion to the increase in mass.

Alternatively, seed of the invention in which AP2 expression is enhanced will have the expression cassettes of the invention and decreased seed mass. Seed mass will be at least about 20% less than the average seed mass of plants of the same variety that lack the expression cassette. Often the mass will be about 50% less and preferably at least about 75% less or the seed will be absent. As above, decreases in other properties e.g., protein and oil will be proportional to the decreases in mass.

The following Examples are offered by way of illustration, not limitation.

EXAMPLE 1

AP2 Gene Isolation

The isolation and characterization of an AP2 gene from Arabidopsis is described in detail in Jofuku et al., supra. Briefly, T-DNA from Agrobacterium was used as an insertional mutagen to identify and isolate genes controlling flower formation in Arabidopsis. One transformsed line, designated T10, segregated 3 to 1 for a flower mutant that phenotypically resembled many allelic forms of the floral homeotic mutant ap2. T10 was tested and it was confirmed genetically that T10 and ap2 are allelic. The mutant was designated as ap2-10.

It was determined that ap2-10 was the product of a T-DNA insertion mutation by genetic linkage analysis using the T-DNA-encoded neomycin phosphotransferase II (NPTII) gene as a genetic marker. An overlapping set of T-DNA-containing recombinant phage was selected from an ap2-10 genome library and the plant DNA sequences flanking the T-DNA insertion element were used as hybridization probes to isolate phage containing the corresponding region from a wild-type Arabidopsis genome library. The site of T-DNA insertion in ap2-10 was mapped to a 7.2-kb EcoR1 fragment centrally located within the AP2 gene region.

Five Arabidopsis flower cDNA clones corresponding to sequences within the 7.2-kb AP2 gone region were isolated. All five cloned cDNAs were confirmed to represent AP2 gene transcripts using an antisense gene strategy to induce ap2 mutant flowers in wild-type plants.

To determine AP2 gene structure, the nucleotide sequences of the cDNA inserts were compared to that of the 7.2-kb AP2 genomic fragment. These results showed that the AP2 gene is 2.5 kb in length and contains 10 exons and 9 introns that range from 85 to 110 bp in length. The AP2 gene encodes a theoretical polypeptide of 432 amino acids with a predicted molecular mass of 48 kD. The AP2 nucleotide and predicted protein sequences were compared with a merged, nonredundant data base. It was found that AP2 had no significant global similarity to any known regulatory protein.

Sequence analysis, however, did reveal the presence of several sequence features that may be important for AP2 protein structure or function. First, AP2 contains a 37-amino acid serine-rich acidic domain (amino acids 14 to 50) that is analogous to regions that function as activation domains in a number of RNA polymerase II transcription factors. Second, AP2 has a highly basic 10-amino acid domain (amino acids 119 to 128) that includes a putative nuclear localization sequence KKSR suggesting that AP2 may function in the nucleus. Finally, that the central core of the AP2 polypeptide (amino acids 129 to 288) contains two copies of a 68-amino acid direct repeat that is referred to here as the AP2 domain. The two copies of this repeat, designated AP2-R1 and AP2-R2, share 53% amino acid identity and 69% amino acid homology. FIG. 1A shows that each AP2 repeat contains an 18-amino acid conserved core region that shares 83% amino acid homology. FIG. 1B shows that both copies of this core region are theoretically capable of forming amphipatlic α-helical structures that may participate in protein-protein interactions.

EXAMPLE 2

Preparation of AP2 Constructs

Figure 2:
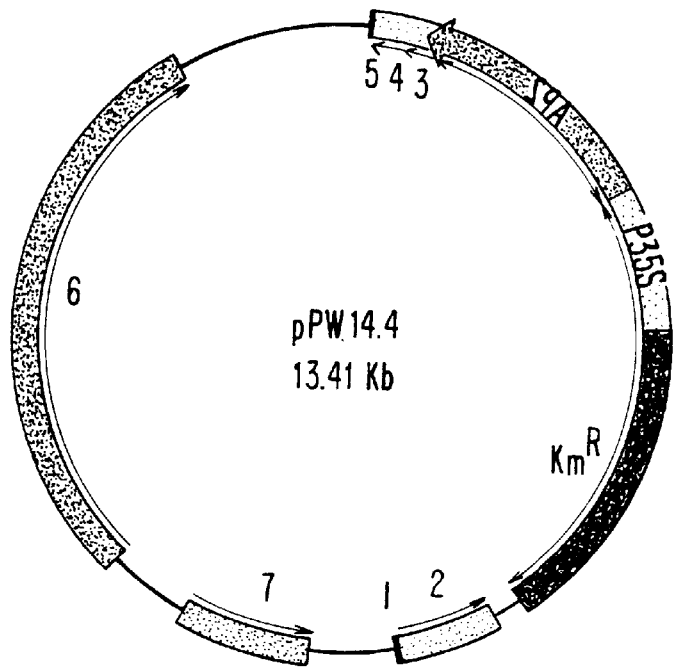
FIG. 2 shows an antisense construct of the invention. pPW14.4 (which is identical to pPW15) represents the 13.41 kb AP2 antisense gene construct used in plant transformation described here. pPW14.4 is comprised of the AP2 gene coding region in a transcriptional fusion with the cauliflower mosaic virus 35S (P35S) constitutive promoter in an antisense orientation. The Ti plasmid vector used is a modified version of the pGSJ780A vector (Plant Genetic Systems, Gent, Belgium) in which a unique EcoR1 restriction site was introduced into the BamH1 site using a Cla1-EcoR1-BamH1 adaptor. The modified pGSJ780A vector DNA was linearized with EcoR1 and the AP2 coding region inserted as a 1.68 kb EcoR1 DNA fragment from AP2 cDNA plasmid cAP2#1 (Jofuku et al., 1994) in an antisense orientation with respect to the 35S promoter. KmR represents the plant selectable marker gene NPTII which confers resistance to the antibiotic kanamycin to transformed plant cells carrying an integrated 35S-AP2 antisense gene. Boxes 1 and 5 represent the T-DNA left and right border sequences, respectively, that are required for transfer of T-DNA containing the 35S-AP2 antisense gene construct into the plant genome. Regions 2 and 3 contain T-DNA sequences. Box 3 designates the 3' octopine synthase gene sequences that function in transcriptional termination. Region 6 designates bacterial DNA sequences that function as a bacterial origin of replication in both *E. coli* and Agrobacterium tumefaciens, thus allowing pPW14.4 plasmid replication and retention in both bacteria. Box 7 represents the bacterial selectable marker gene that confers resistance to the antibiotics streptomycin and spectinomycin and allows for selection of Agrobacterium strains that carry the pPW14.4 recombinant plasmid.
Figure 3:
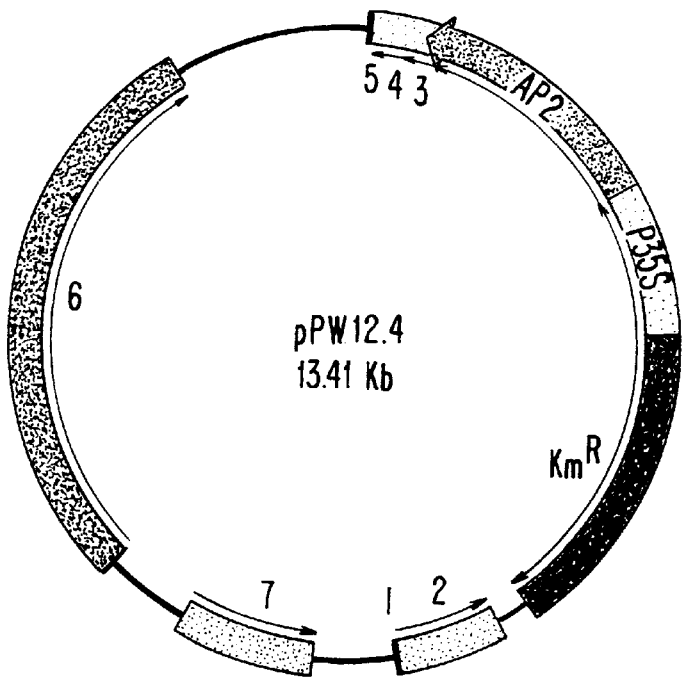
FIG. 3 shows a sense construct of the invention. pPW12.4 (which is identical to pPW9) represents the 13.41 kb AP2 sense gene construct used in plant transformation described here. pPW12.4 is comprised of the AP2 gene coding region in a transcriptional fusion with the cauliflower mosaic virus 35S (P35S) constitutive promoter in a sense orientation. The Ti plasmid vector used is a modified version of the pGSJ780A vector (Plant Genetic Systems, Gent, Belgium) in which a unique EcoR1 restriction site was introduced into the BamH1 site using a Cla1-EcoR1-BamH1 adaptor. The modified pGSJ780A vector DNA was linearized with EcoR1 and the AP2 coding region inserted as a 1.68 kb EcoR1 DNA fragment from AP2 cDNA plasmid cAP2#1 (Jofuku et al., 1994) in a sense orientation with respect to the 35S promoter. KmR represents the plant selectable marker gene NPTII which confers resistance to the antibiotic kanamycin to transformed plant cells carrying an integrated 35S-AP2 antisense gene. Boxes 1 and 5 represent the T-DNA left and right border sequences, respectively, that are required for transfer of T-DNA containing the 35S-AP2 sense gene construct into the plant genome. Regions 2 and 3 contain T-DNA sequences. Box 3 designates the 3' octopine synthase gene sequences that function in transcriptional termination. Region 6 designates bacterial DNA sequences that function as a bacterial origin of replication in both *E. coli* and Agrobacterium tumefaciens, thus allowing pPW12.4 plasmid replication and retention in both bacteria. Box 7 represents the bacterial selectable marker gene that confers resistance to the antibiotics streptomycin and spectinomycin and allows for selection of Agrobacterium strains that carry the pPW12.4 recombinant plasmid.

Gene constructs were made comprising the AP2 gene coding region described above in a transcriptional fusion with the cauliflower mosaic virus 35S constitutive promoter in both the sense and antisense orientations. Tile original vector containing the 35S promoter pGSJ780A was obtained from Plant Genetic Systems (Gent, Belgium). The PGSJ780A vector was modified by inserting a Cla1-BamH1 adaptor containing an EcoR1 site in the unique BamH1 site of PGSJ780A. The modified PGSJ780A DNA was linearized with EcoR1 and the AP2 gene coding region inserted as a 1.68 kb EcoR1 fragment in both sense and antisense orientations with respect to the 35S promoter (see, FIGS. 2 and 3).

The resultant DNA was transformed into E. coli and spectinomycin resistant transformants were selected. Plasmid DNAs were isolated from individual transformants and the orientation of the insert DNAs relative to the 35S promoter were confirmed by DNA sequencing. Bacterial cells containing the 35S/AP2 sense (designated pPW12.4 and pPW9) and 35S/AP2 antisense (designated pPW14.4 and pPW15) constructs were conjugated to Agrobacterium tumefaciens and rifampicin, spectinomycin resistant transformants were selected for use in Agrobacterium-mediated plant transformation experiments.

The 35S/AP2 sense and 35S/AP2 antisense constructs were introduced into wild-type Arabidlopsis and tobacco plants according to standard techniques. Stable transgenic plant lines were selected using the plant selectable marker NPTII (which confers resistance to the antibiotic kanamycin) present on the modified Ti plasmid vector PGSJ780A.

EXAMPLE 3

Modification of Seed Using AP2 Sequences

This example shows that ap2 mutant plants and transgenic plants containing the 35S/AP2 antisense construct produced seed with increased mass and total protein content. By contrast, transgenic plants containing the 35S/AP2 sense construct produced seed with decreased mass and protein content. Together these results indicate that seed mass and seed contents in transgenic plants can be modified by genetically altering AP2 activity.

Seed from 30 lines were analyzed for altered seed size and seed protein content including the Arabidopsis ap2 mutants ap2-1, ap2-3, ap2-4, ap2-5, ap2-6, ap2-9 and ap2-10 and transgenic Arabidopsis and transgenic tobacco containing the CaMV 35S/AP2 antisense gene construct, the CaMV 35S/AP2 sense gene construct, or the pGSJ780A vector as described above. The ap2 mutants used in this study are described in Komaki et al., *Development* 104, 195–203 (1988), Kunst et al., Plant Cell 1, 1195–1208 (1989), Bowman et al., *Development* 112, 1–20 (1991), and Jofuku et al., supra.

Due to the small size of Arabidopsis and tobacco seed, average seed mass was determined by weighing seed in batches of 100 for Arabidopsis and 50 seed for tobacco. The net change in seed mass due to changes in AP2 gene activity was calculated by subtracting the average mass of wild-type seed from mutant seed mass.

Seed from three wild-type Arabidopsis ecotypes C24, Landsberg-er , and Columbia, and one wild-type tobacco SR1 were used as controls. Wild-type Arabidopsis seed display seasonal variations in seed mass which range from 1.6–2.3 mg per 100 seed as shown in Table I. Therefore transgenic Arabidopsis seed were compared to control seed that had been harvested at approximately the same time of season. This proved to be an important for comparing the effects of weak ap2 mutations on seed mass.

Table I shows that all ap2 mutant seed examined, ap2-1, ap2-3, ap2-4, ap2-5, ap2-6, ap2-9, and ap2-10, show a significant increase in average seed mass ranging from +27 to +104 percent compared to wild-type. The weak partial loss-of-function mutants such as ap2-1 and ap2-3 show the smallest gain in average seed mass ranging from +27 percent to +40 percent of wild-type, respectively. By contrast, strong ap2 mutants such as ap2-6 and ap2-10 show the largest gain in seed mass ranging from +69 percent to +104 percent of wild-type, respectively. Thus reducing AP2 gene activity genetically consistently increases Arabidopsis seed mass.

AP2 antisense and AP2 sense cosuppression strategies described above were used to reduce AP2 gene activity in planta to determine whether seed mass could be manipulated in transgenic wild-type plants. Twenty-nine independent lines of transgenic Arabidopsis containing the CaMV 35S/AP2 antisense gene constructs pPW14.4 and pPW15 (FIG. 2) were generated. Each transgenic line used in this study tested positive for kanamycin resistance and the presence of one or more copies of T-DNA.

Table I shows that seed from nine transgenic Arabidopsis AP2 antisense lines show a significant increase in seed mass when compared to control seed ranging from +22 percent for line C24 15-542 to +89 percent for line C24 15-566. Both C24 and Landsberg-er ecotypes were used successfully. Increased seed mass was observed in F1, F2, and F3 generation seed.

Eight lines containing the 35S/AP2 sense gene construct were generated which were phenotypically cosuppression mutants. As shown in Table I seed from two cosuppression lines examined showed larger seed that range from +26 percent to +86 percent. By contrast, plants transformed with the vector pGSJ780A showed a normal range of average seed mass ranging from −0.5 percent to +13 percent compared to wild-type seed (Table I). Together, these results demonstrate that AP2 gene sequences can be used to produce a significant increase in Arabidopsis seed mass using both antisense and cosuppression strategies in a flowering plant.

TABLE I

Genetic control of Arabidopsis seed mass by AP2.

|  | Average seed mass in mg per 100 seed[1,2] | Percent change in seed mass compared to wild-type |
|---|---|---|
| ap2 mutant seed | 2.1 (0.1) | +27% |
| 1. ap2-1 | 2.2 (0.1) | +33% |
|  | 2.1 (0.2) | +31% |
|  | 2.8 (0.2) | +33% |
| 2. ap2-3 | 2.6 (0.1) | +27% |
| 3. ap2-4 | 3.5 (0.3) | +69% |
|  | 3.5 (0.2) | +69% |
| 4. ap2-5 | 2.9 (0.1) | +39% |
| 5. ap2-6 | 3.5 (0.2) | +69% |
| 6. ap2-9 | 2.9 (0.1) | +40% |
| 7. ap2-10 | 3.7 (0.4) | +79% |
|  | 3.9 (0.3) | +90% |
|  | 4.2 (0.5) | +104% |
| Seed produced by transgenic CaMV35S/AP2 antisense lines (from a Km resistant mother) |  |  |
| 1. C24 14.4E (F1-15) F2 sd | 3.1 | +35% |
| C24 14.4E (F1-15) F3 sd | 3.4 (0.3) | +47% |
| 2. C24 14.4S (F1-1) | 2.8 (0.2) | +29% |
| 3. C24 14.4AA (F1-24) | 2.9 (0.1) | +30% |
| 4. C24 14.4DD (F1-2) | 2.8 (0.3) | +30% |
| 5. C24 15-522 | 3.6 (0.1) | +76% |
| 6. C24 15-542 (F1-2) | 2.6 (0.1) | +25% |
| C24 15-542 (F1-7) | 2.5 (0.2) | +22% |
| 7. C24 15-566 | 3.9 (0.1) | +89% |
| 8. LE 15-9992-3 (F1-1) F2 sd | 2.4 (0.1) | +42% |
| 9. LE 15-83192-3 (F1-3) | 2.8 (0.0) | +33% |
| LE 15-83192-3 (F1-17) | 2.7 (0.0) | +28% |
| Seed produced by transgenic CaMV35S/AP2 cosuppression lines (from a Km resistant mother) |  |  |
| 1. C24 9-5 (F1-5) | 3.8 (0.0) | +86% |
| 2. LE 9-83192--2 (F1-19) | 2.7 (0.2) | +26% |
| LE 9-83192-2 (F1-24) | 2.7 (0.1) | +26% |
| Seed produced by transgenic pGSJ780A vector only lines (from a Km resistant mother plant) |  |  |
| 1. C24 3-107 (F1-1) | 2.2 (0.1) | +9% |
| 2. C24 3-109 (F1-1) | 2.3 (0.0) | +13% |
| 3. LE 3-83192-1 (F1-2) | 2.3 (0.1) | +7% |
| 4. LE 3-83192-3 (F1-2) | 2.4 (0.1) | +11% |
| 5. LE 3-9992-4 (F1-4) | 2.4 (0.2) | +12% |
| LE 3-9992-4 (F1-6) | 2.3 (0.0) | +9% |
| LE 3-9992-4 (F1-8) | 2.1 (0.0) | −0.5% |
| 6. LE 3-9992-9 (F1-3) | 2.3 (0.1) | +7% |
| Seed produced by wild-type Arabidopsis plants |  |  |
| 1. C24 | 2.0 (0.1) |  |
|  | 2.3 (0.1) |  |
|  | 2.2 |  |
| 2. Landsberg-er | 1.6 (0.1) |  |
|  | 2.1 (0.1) |  |
|  | 2.1 |  |
|  | 2.3 (0.1) |  |
| 3. Columbia | 1.8 (0.1) |  |
|  | 2.1 (0.1) |  |

[1]Standard deviation values are given in parentheses.
[2]Wild-type seed values used for this comparison were chosen by ecotype and harvest date.

Arabidopsis AP2 gene sequences were also used to negatively control seed mass in tobacco, a heterologous plant species. Table II shows that in five transgenic tobacco lines the CaMV 35S/AP2 overexpression gene construct was effective in reducing transgenic seed mass from −27 percent to −38 percent compared to wild-type seed. These results demonstrate the evolutionary conservation of AP2 gene function at the protein level for controlling seed mass in a heterologous system.

TABLE II

Genetic control of tobacco seed mass using Arabidopsis AP2.

|  | Average seed mass in mg per 5 seed[1] | Percent change in seed mass compared to wild-type |
|---|---|---|
| Seed produced by transgenic CaMV 35S/AP2 sense gene lines (from a Km resistant mother) |  |  |
| 1. SR1 9-110 To | 3.1 (0.0) | −27% |
| SR1 9-110 (F1-5) | 3.0 (0.2) | −29% |
|  | 2.8 (0.3) | −34% |
| 2. SR1 9-202 (F1-G) | 3.1 (0.2) | −27% |
| SR1 9-202 (F1-I) | 3.2 (0.1) | −24% |
| 3. SR1 9-103 (F1-2) | 3.9 (0.0) | −8% |

TABLE II-continued

Genetic control of tobacco seed mass using Arabidopsis AP2.

| | Average seed mass in mg per 5 seed[1] | Percent change in seed mass compared to wild-type |
|---|---|---|
| 4. SR1 9-413-1 | 2.8 (0.0) | −34% |
| | 3.0 (0.2) | −29% |
| 5. SR1 9-418-1 To | 3.5 (0.1) | −18% |
| Seed produced by transgenic CaMV 35S/AP2 antisense gene lines (from a Km resistant mother) | | |
| 1. SR1 15-111 | 5.1 (0.4) | +20% |
| SR1 15-111 (F1) | 5.0 (0.4) | +19% |
| 2. SR1 15-116 To | 4.1 (0.4) | −3% |
| SR1 15-116 (F1-2) | 4.0 (0.1) | −5% |
| SR1 15-116 (F1-1) | 4.5 (0.1) | +5% |
| 3. SR1 15-407 (F1) | 4.8 (0.5) | +10% |
| | 4.7 (0.3) | +10% |
| 4. SR1 15-102 (F1) | 4.5 (0.2) | +6% |
| 5. SR1 15-413 (F1-3) | 4.2 (0.0) | +0% |
| 6. SR1 15-410 (F1-2) | 4.4 (0.0) | +4% |
| 7. SR1 15-210 (F1-4) | 3.6 (0.1) | −15% |
| Seed produced by pGSJ780A vector only lines (from a Km resistant mother) | | |
| 1. SR1 3-402 (F1) | 5.0 (0.1) | +17% |
| 2. SR1 3-401 (F1) | 4.6 (0.1) | +8% |
| 3. SR1 3-405 (F1) | 4.4 (0.1) | +4% |
| Seed from wild-type tobacco | | |
| 1. SR1 | 4.2 (0.3) | |
| | 4.0 (0.1) | |

[1]Standard deviation values are given in parentheses.

Use of AP2 Gene Constructs to Control Seed Protein Content

Total seed protein was extracted and quantitated from seed produced by wild-type, ap2 mutant, transgenic AP2 antisense, and transgenic AP2 sense cosuppression plants according to Naito et al. *Plant Mol Biol.* 11, 109–123 (1988). Seed protein was extracted in triplicate from batches of 100 dried seed for Arabidopsis or 50 dried seed for tobacco. Total protein yield was determined by the Bradford dye-binding procedure as described by Bradford, *Anal. Biociem.* 72:248 (1976). The results of this analysis are shown in Table III.

ap2 mutant total seed protein content increased by 20 percent to 78 percent compared to wild-type control seed. Total seed protein from transgenic AP2 antisense plants increased by +31 percent to +97 percent compared to wild-type controls. Transgenic AP2 cosuppression seed showed a +13 and +17 percent increase over wild-type. Together, the transgenic antisense and cosuppression mutant seed consistently yielded more protein per seed than did the wild-type controls or transgenic plants containing the pGSJ780A vector only (Table III).

TABLE III

Genetic control of total seed protein content in Arabidopsis using AP2.

| | Total see protein in μg per 100 seed[1] | Percent change in protein content compared to wild-type |
|---|---|---|
| ap2 mutant seed | | |
| 1. ap2-I | 652 (17) | +20% relative to WT seed |
| | 615 (30) | +11% |
| 2. ap2-3 | 705 (47) | +27% |
| 3. ap2-4 | 729 (107) | +33% |
| 4. ap2-5 | 617 (24) | +13% |
| 5. ap2-6 | 836 (14) | +52% |
| 6. ap2-9 | 798 (11) | +46% |
| 7. ap2-10 | 836 (15) | +78% |
| Transgenic CaMV 35S/AP2 antisense see mass (from Km resistant mother) | | |
| 1. C24 14.4E (F1-1) F3 sd | 615 (60) | +31% |
| 2. C24 15-522 (F1-1) | 790 (23) | +68% |
| 3. C24 15-566 | 925 (173) | +97% |
| Transgenic CaMV 35S/AP2 sense cosuppression seed mass (from Km Resistant mother plant) | | |
| 1. LE 9-83192-2 (F1-19) | 616 | +13% |
| LE 9-83192-2 (F1-24) | 637 | +17% |
| Wild-type seed | | |
| 1. C24 | 469 (19) | |
| 2. LE | 545 (22) | |
| | 555 | |
| 3. Col | 548 (42) | |

[1]Standard deviation values are given in parentheses.

Transgenic tobacco containing the 35S/AP2 sense gene construct show that AP2 overexpression can decrease seed protein content by 27 to 45 percent compared to wild-type seed. Together, the transgenic Arabidopsis and tobacco results demonstrate that seed mass and seed protein production can be controlled by regulating AP2 gene activity.

TABLE IV

Negative control of transgenic tobacco seed protein content by Arabidopsis AP2 gene expression.[1]

| | Ave. protein per 50 seed | Percent change in protein content compared to wild-type |
|---|---|---|
| Seed produced by transgenic CAMV 35S/AP2 sense gene plant | | |
| 1. SR1 9-110 | 242 (11) | −45% |
| 2. SR1 9-202 (F1-G) | 271 (11) | −38% |
| 3. SR1 9-413 | 362 (8) | −18% |
| 4. SR1 9-418-1 | 319 (16) | −27% |
| Wild-type Control | | |
| SR1 (wild-type) | 440 (8) (JO) | NA |

[1]Standard deviation values are given in parentheses.

Analysis of Transgenic Seed Proteins by Gel Electrophoresis

Arabidopsis seed produce two major classes of seed storage proteins, the 12S cruciferins and 2S napins which are structurally related to the major storage proteins found in the Brassicaceae and in the Leguminoceae. The composition of seed proteins in wild-type, ap2 mutant, and transgenic Arabidopsis seed were compared by SDS polyacrylamide gel electrophoresis as described by Naito et al., *Plant Mol. Biol.* 11, 109–123 (1988). Total seed proteins were extracted as described above. 50 μg aliquots were separated by gel electrophoresis and stained using Coomassie brilliant blue. These results showed that the spectrum of proteins in wild-type and ap2 mutant seed are qualitatively indistinguishable. There is no detectable difference in the representation of the 12S or 2S storage proteins between the wild-type and ap2 mutant seed extracts. This shows that reducing AP2 gene activity genetically does not alter the profile of storage proteins synthesized during seed maturation. The spectrum of seed proteins produced in transgenic AP2 antisense and AP2 sense cosuppression seed are also indistinguishable from wild-type. In particular, there is no detectable difference in the representation of the 12S cruciferin or 2S napin storage proteins in the larger seed.

Finally, the transgenic tobacco plants containing the 35S/AP2 overexpression gene construct produced significantly smaller seed. Despite the decrease in seed mass in transgenic tobacco there was no detectable difference in storage protein profiles between seed from 35S/AP2 transformants and wild-type SR1.

AP2 Acts Maternally to Control Seed Size

We carried out reciprocal crosses using ap2-10 and wild-type plants to determine whether AP2 functions through the maternal or the embryonic genomes to control seed mass. Table IV shows that seed produced by ap2-10 flowers pollinated using WT pollen were greater than 2× larger than seed produced by WT plants using ap2-10 pollen. The heterozygous seed produced by ap2-10 plants displayed the distinctive ap2 seed coat phenotype described by Jofuku et al., supra. By contrast, seed produced by WT flowers pollinated with ap2-10 pollen were comparable in mass to homozygous WT seed and had a normal seed coat (Table V). These results show that AP2 controls seed development through the maternal genome and genetically implicate the seed coat as one important site for AP2 regulatory gene activity.

TABLE V

Maternal control of average seed mass.

| Cross ♀ × ♂ | | Average mass per 100 seed[1] |
|---|---|---|
| 1. ap2-10 | WT | 6.1 (0.6) |
| 2. WT | ap2-10 | 2.2 (0.1) |
| 3. ap2-10 | ap2-10 | 4.2 (0.5) |
| 4. WT | WT | 2.3 (0.1) |

[1]Standard deviation values are given in parentheses.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

---

What is claimed is:

1. A method of modulating seed mass in a plant, the method comprising:
   providing a first plant comprising a recombinant expression cassette containing an AP2 nucleic acid linked to a plant promoter, which AP2 nucleic acid that hybridizes under stringent conditions to SEQ ID NO:3;
   selfing the first plant or crossing the first plant with a second plant, thereby producing a plurality of seeds; and
   selecting seed with altered mass.

2. The method of claim 1, wherein expression of the AP2 nucleic acid inhibits expression of an endogenous AP2 gene and the step of selecting includes the step of selecting seed with increased mass.

3. The method of claim 2, wherein the seed have increased protein content, carbohydrate content, or oil content.

4. The method of claim 2, wherein the AP2 nucleic acid is linked to the plant promoter in the antisense orientation.

5. The method of claim 2, wherein the seed is set on the first plant.

6. The method of claim 2, wherein the first and second plants are the same species.

7. The method of claim 2, wherein the first and second plants are members of the family Brassicaceae.

8. The method of claim 2, wherein the first and second plants are members of the family Solanaceae.

9. The method of claim 2, wherein the plant promoter is a constitutive promoter.

10. The method of claim 9, wherein the promoter is a CaMV 35S promoter.

11. The method of claim 2, wherein the promoter is a tissue-specific promoter.

12. The method of claim 11, wherein the promoter is fruit-specific, ovule-specific, seed-specific, integument-specific, or seed coat-specific.

13. A seed produced by the method of claim 2.

14. The method of claim 1, wherein expression of the AP2 nucleic acid enhances AP2 activity and the step of selecting includes the step of selecting seed with decreased mass.

15. The method of claim 14, wherein the seed is set on the first plant.

16. The method of claim 14, wherein the first and second plants are the same species.

17. The method of claim 14, wherein the first and second plants are members of the family Brassicaceae.

18. The method of claim 14, wherein the first and second plants are members of the family Solanaceae.

19. The method of claim 14, wherein the plant promoter is a constitutive promoter.

20. The method of claim 19, wherein the promoter is a CaMV 35S promoter.

21. The method of claim 14, wherein the promoter is a tissue-specific promoter.

22. The method of claim 21, wherein the promoter is fruit-specific, ovule-specific, seed-specific, integument-specific, or seed coat-specific.

23. A seed produced by the method of claim 14.

24. A seed comprising a recombinant expression cassette containing an AP2 nucleic acid, which hybridizes under stringent conditions to SEQ ID NO:3.

25. The seed of claim 24, which is derived from a plant that is a member of the family Brassicaceae.

26. The seed of claim 24, wherein the AP2 nucleic acid is linked to a plant promoter in an antisense orientation and the seed mass is at least about 10% greater than the average mass of seeds from the same plant variety which lack the recombinant expression cassette.

27. The seed of claim 26, wherein the mass is at least about 20% greater than the average mass of seeds from the same plant variety which lack the recombinant expression cassette.

28. The seed of claim 26, wherein the mass is at least about 50% greater than the average mass of seeds from the same plant variety which lack the recombinant expression cassette.

29. The seed of claim 26, wherein the oil content is proportionally increased.

30. The seed of claim 26, wherein the protein content is proportionally increased.

31. The seed of claim 24, wherein the AP2 nucleic acid is linked to a plant promoter in the sense orientation and the seed mass is at least about 10% less than the average mass of seeds of the same plant variety which lack the recombinant expression cassette.

32. The seed of claim 31, which has a mass at least about 20% less than the average mass of seeds of the same plant variety which lack the recombinant expression cassette.

33. The seed of claim 31, which has a mass at least about 50% less than the average mass of seeds of the same plant variety which lack the recombinant expression cassette.

34. The method of claim 2, wherein the AP2 nucleic acid is linked to the promoter in the sense orientation.

35. The method of claim 1, wherein the AP2 nucleic acid encodes an AP2 polypeptide having an AP2 domain as shown in SEQ ID NO:1 or SEQ ID NO:2.

* * * * *

UNITED STATES PATENT AND TRADEMARK OFFICE
CERTIFICATE OF CORRECTION

PATENT NO.    : 5,994,622
DATED         : November 30, 1999
INVENTOR(S)   : K. Diane Jofuku and Jack K. Okamuro It is certified that error appears in the above-identified patent and that said Letters Patent is hereby corrected as shown below:

Column 1,
Line 2, please insert the following statement:
-- This invention was made with Government support under Grant Nos. GM08132 and GM46309, awarded by the National Institutes of Health. The Government has certain in this invention. --

Signed and Sealed this

Fourteenth Day of January, 2003

JAMES E. ROGAN
*Director of the United States Patent and Trademark Office*